US006187838B1

(12) United States Patent
Dickens

(10) Patent No.: US 6,187,838 B1
(45) Date of Patent: Feb. 13, 2001

(54) POLYMERIZABLE CONDITIONERS FOR ADHESIVE BONDING TO DENTIN AND ENAMEL

(75) Inventor: Sabine H. Dickens, Gaithersburg, MD (US)

(73) Assignee: American Dental Association Health Foundation, Chicago, IL (US)

(*) Notice: Under 35 U.S.C. 154(b), the term of this patent shall be extended for 0 days.

(21) Appl. No.: 09/327,180

(22) Filed: Jun. 7, 1999

Related U.S. Application Data

(62) Division of application No. 08/785,174, filed on Jan. 13, 1997, now Pat. No. 6,001,897.

(51) Int. Cl.[7] .......................... A61K 6/283; C08F 20/10
(52) U.S. Cl. ...................... 523/118; 523/116; 524/547; 524/559; 526/277; 526/278; 526/318.1; 433/228.1; 206/63.5
(58) Field of Search .................................. 523/116, 118; 524/547, 559; 526/277, 278, 318.1; 433/228.1; 206/63.5

(56) References Cited

U.S. PATENT DOCUMENTS

| | | |
|---|---|---|
| 4,368,043 | 1/1983 | Yamauchi et al. . |
| 4,514,342 | 4/1985 | Billington et al. .................... 260/952 |
| 4,514,527 | 4/1985 | Bowen ................................ 523/115 |
| 4,553,941 | 11/1985 | Aasen ................................ 433/228.1 |
| 4,657,941 | 4/1987 | Blackwell et al. ...................... 522/14 |
| 4,719,149 | 1/1988 | Aasen et al. ........................... 428/473 |
| 4,814,423 | 3/1989 | Huang et al. .......................... 528/230 |
| 4,816,495 | 3/1989 | Blackwell et al. ...................... 522/14 |
| 4,880,660 | 11/1989 | Aasen et al. .............................. 427/2 |
| 4,936,775 | 6/1990 | Bennett ................................ 433/220 |
| 4,966,934 | 10/1990 | Huang et al. . |
| 5,089,051 | 2/1992 | Eppineer et al. . |
| 5,264,513 | 11/1993 | Ikemura et al. . |
| 5,270,351 | * 12/1993 | Bowen . |
| 5,320,886 | 6/1994 | Bowen ................................ 428/34.1 |
| 5,348,988 | 9/1994 | Suh et al. .............................. 523/118 |
| 5,374,664 | 12/1994 | Zalsman et al . . |
| 5,525,648 | 6/1996 | Aasen et al. .......................... 523/116 |
| 5,530,038 | * 6/1996 | Yamamoto et al. . |
| 5,554,030 | 9/1996 | Ario et al. ............................. 433/226 |
| 5,658,963 | * 8/1997 | Qian et al. . |
| 5,739,177 | 4/1998 | Ohno et al. . |

OTHER PUBLICATIONS

M. Anbar, et al., "Potential Use of Organic Plyphosphonates as Adhesive in the Restoration of Teeth" *Organic Polyphosphonates,* 53(4):879–888 (1974).

M. Anbar, et al., "Organic Polymeric Polyphosphonates as Potential Preventive Agents of Dental Caries: In Vitro Experiments", *Anbar, St. John, and Scott,* 53:(4):876–878 (1974).

B. Van Meerbeek, et al., "Correlative Transmission Electron Microscopy Examination of Nondemineralized and Demineralized Resin–Dentin Interfaces Formed by Two Dentin Adhesive Systems", *TEM evaluation of Two Dentin Adhesive,* 75:(3) 879–888 (1996).

Tadao Fukushima, et al., "Application of Functional Monomers for Dental Use (Part–9) Syntheses of Succinoxy Methacrylates and Their Adhesion to Polished and Etched Tooth Surfaces", *Dental Materials Journal,* 4:(1) 31–39 (1985).

I. Watanabe, et al., "Bonding to Ground Dentin by a Phenyl–P Self–etching Primer", *J. Dent Res.,* 73(6) 1212–1220 (1994).

Israel Cabasso, et al., "Acrylated phosphonate esters containing . . . ", *Journal of Biomedical Materials Research,s,* 24 705–720 (1990).

T. Inoue, et al., "Effect of Self–etching primer on Bonding of light–cured Composite Resin to Polished Dentin", *Abstract,* 992 (1994).

S. Venz, et al., "Modified Surface–active Monomers for Adhesive Bonding to Dentin, " J. Dent Res. 72(3):582–586 (1993).

H. Ralph Rawls, et al., "Adsorption of Phosphonylated Polyelectrolytes on Hydroxyapatite", 115–128.

\* cited by examiner

*Primary Examiner*—Peter A. Szekely
(74) *Attorney, Agent, or Firm*—Banner & Witcoff, Ltd.

(57) ABSTRACT

The use of polymerizable monomeric conditioning agents for treating the enamel and dentin of a tooth prior to application of a primer and subsequent application of a bonding resin, or a combination of a primer/bonding resin has been found to provide good shear bond strength on both moist and dry dentin. In addition, the contact angles provided by water on dentin conditioned with the polymerizable conditioners as compared to the non-polymerizable phosphoric acid are much lower, reflecting improved spreading over the surface of the tooth.

24 Claims, 12 Drawing Sheets

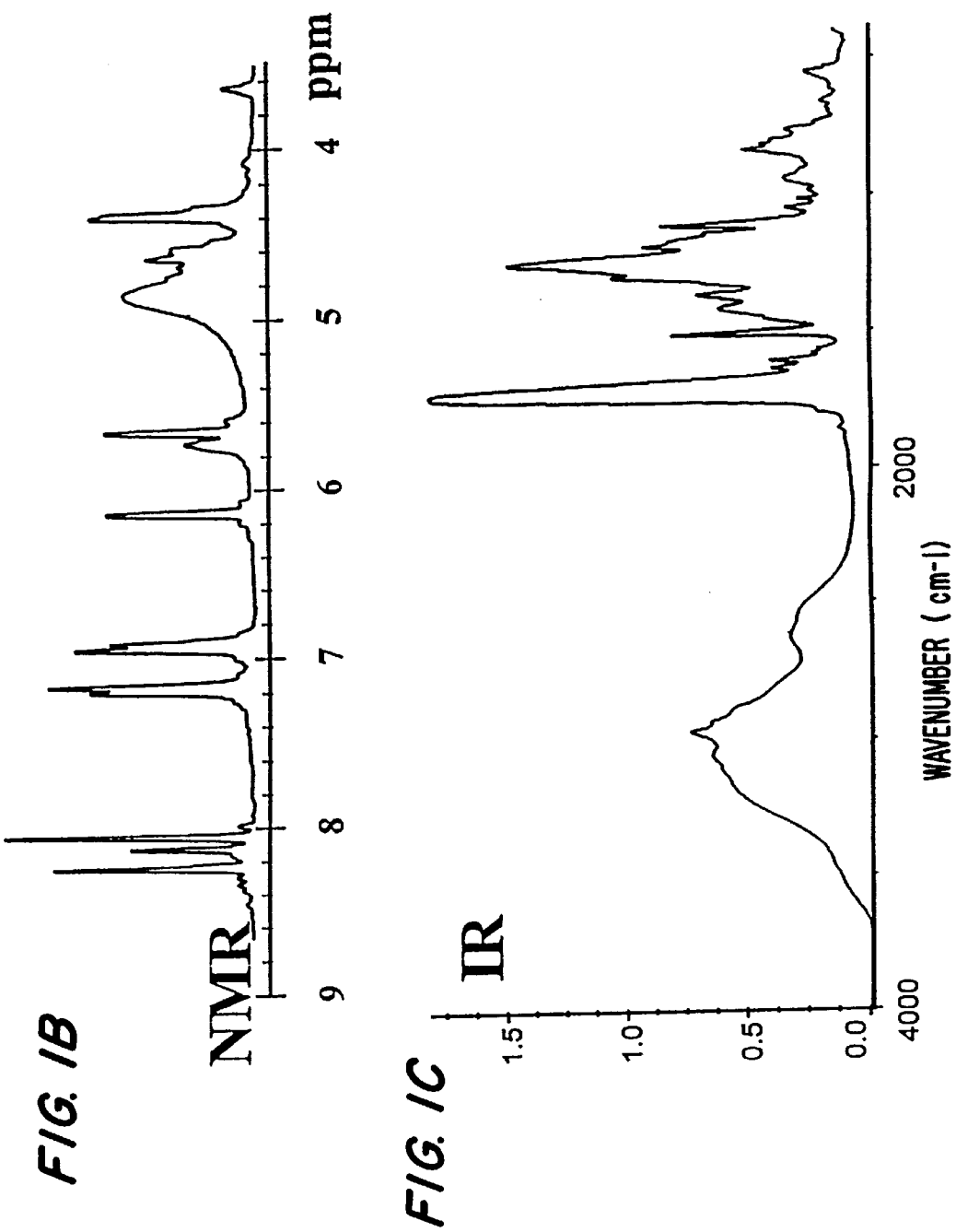

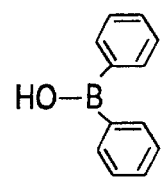
diphenylborinic acid
(DFB)

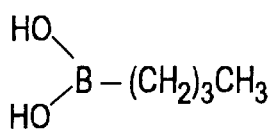
n-butylboronic acid
(BUTB)

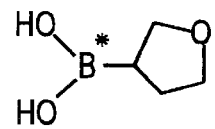
diethanolamine-
tetrahydrofuranylboronate
(RDETHFB & SDETHFB)

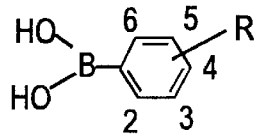

| POSITION | R | CODE | POSITION | R | CODE |
|---|---|---|---|---|---|
| – | NONE | 2FDB* | 4 | B(OH)$_2$ | B14DA |
| 2 | –CHO | 2FORMB* | 4 | –OCH$_3$ | 4MEOB |
|  |  |  | 4 | –CHO | 4FORMB |
| 3 | –CF$_3$ | 3TFMB | 4 | –CF$_3$ | 4TFMB |
|  |  |  | 4 | –Br | 4BPB |
| 3 | –NHSO$_2$–naphthyl–N(Me)$_2$ | NSULFB* | 4 | –C$_6$H$_4$–B(OH)$_2$ | BIPD |
| 3 | –NO$_2$ | 3NPB* | 2,5 | 2: –OH  5: –N=N–C$_6$H$_4$–CF$_3$ | HFAB |
| 3 | –NH$_2$ | MAPB* |  |  |  |
| 4 | –CH$_3$ | 4MEPB* |  |  |  |
| 4 | –CO$_2$H | 4COOHB | 2,5 | 2: –OH  5: –N=N–C$_6$H$_4$–Br | 4BPAPB |
| 4 | –F | 4FB |  |  |  |

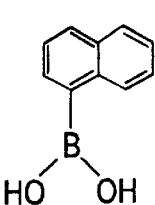
1-napthalene-
boronic acid
(NAPB)

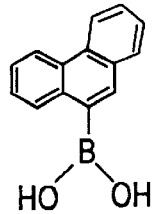
9-phenanthrene-
boronic acid
(9PHNB)

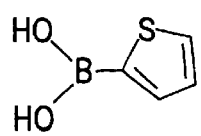
thiophene-2-
boronic
acid (TH2B)

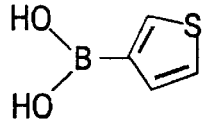
thiophene-3-
boronic
acid (TH3B)

FIG. 1D 3-formylthiophene-2-
boronic acid (3FTH2B)

5-chlorothiophene-2
boronic acid (5CLTH2B)

5-acetylthiophene-2
boronic acid (5ACTH2B)

benzo[b]thiophene-2
boronic acid (5ZBTH2B)

benzo[b]furan-2 boronic
acid (BZBF2B)

POLYMERIZABLE CONDITIONERS FOR ADHESIVE BONDING TO DENTIN AND ENAMEL

This application is a divisional of U.S. Ser. No. 08/785,174, filed Jan. 13, 1997, now U.S. Pat. No. 6,001,897.

This invention was made under National Institute of Dental Research grant R37 DE05129 from the National Institutes of Health. The government therefore retains certain rights in the invention.

BACKGROUND OF THE INVENTION

Most current bonding systems use chelating or mineral acids to remove the mineral from the smear layer and from the intact subsurface dentin in order to enhance penetration of the primer and the formation of a hybridized dentin layer (Nakabayashi, 1982). Demineralization by acids may be responsible for destabilization of the mineral-depleted collagen (Scott and Leaver, 1974; Okamoto et al., 1991). Bonding of composite restoratives with acetone-based, carboxylic acid-containing adhesives and a water-based primer to such acid-conditioned dentin dried after conditioning and rinsing results in significantly lower shear bond strengths (SB S) than bonding to dentin kept moist after conditioning (Kanca, 1992; Gwinnett, 1992; Racean et al., 1992; Swift and Triolo, 1992; Dickens, 1995).

Drying of dentin after conditioning with acids has been shown by scanning and transmission electron microscopy (SEM, TEM) to result in collapsed surface collagen (Sugizaki 1991; Inokoshi et al., 1993; Gwinnett, 1994; Dickens, 1995). Pashley (1993) reported that conditioning hard tissues with aqueous phosphoric acid ($H_3PO_4$) and a subsequent drying step caused reduced porosity of the upper demineralized dentin and produced a dense collagen crust. He also observed that collagen collapsed to a certain degree even on surfaces that had been kept moist after conditioning and hypothesized that the surrounding water, although hydrogen-bonded to the collagen, was not strong enough to support the mineral-depleted collagen in the same way as original dentin mineral.

Various approaches to preventing collapse of surface collagen have been published: Sugizaki (1991) showed that treatment of conditioned, dried dentin with various hydrophllic monomers re-expanded the collapsed collagen to its original level. Conditioning with 10%[1] citric acid containing either 20% calcium chloride or 3% ferric chloride (termed '10-3'), was effective in preventing the collapse of surface collagen (Sugizaki, 1991). Nakabayashi (1985) speculated that ferric chloride suppresses the denaturation of collagen fibers, thereby contributing to higher bond strength. The latter point was supported by Mizunuma (1986), who reported that collagen fibers treated this way are less susceptible to trypsin digestion. The theory was questioned by Imai et al. (1991), who suggested that ferric ions adsorbed onto collagen may act as polymerization initiators and accelerators. TE micrographs of dentin, which had been conditioned with 10-3 and then dried, showed deposition of electron-dense material along extended collagen fibrils (Dickens, 1995) and confirmed Sugizaki's observations. Precipitated Fe- and/or Ca-salts had strengthened the collagen fibrils sufficiently to prevent them from collapsing when dried. When similarly treated specimens were tested in a shear bond test, they still showed significantly lower SBS than specimens for which dentin surfaces were kept moist after conditioning. That suggested that other parameters, e.g., decreased wetting of the dried surface, may have resulted in less complete infiltration of the primer.

Infiltration ofthe primer in the acid-treated dentin surface to a depth less than that altered by the acidic conditioner is thought to be responsible for a potentially weak collagen-rich band between conditioned and unaltered dentin. (Kiyomura, 1987; Nakabayashi 1995; Dickens-Venz et al., 1992; Van Meerbeck et al., 1992; Tam and Pilliar, 1994). Use of acidic polymerizable primers e.g. phenyl-P (2-methacryloyl phenyl hydrogen phosphate) in 2-hydroxyethyl methacrylate (HEMA; Watanabe et al., 1994) or 2-acryloyloxyethyl hydrogen maleate in water (Inoue et al., 1993) without any additional conditioners, was reported to have penetrated throughout the smear layer and formed with the unaltered dentin an acid-proof, hybridized layer.

Several currently used bonding systems use primers based on carboxylic acid monomers (Bowen, 1965; Bowen et al., 1982; Bowen, 1985; Bowen et al.; 1987; Bowen, 1994; Suh et al., 1994), e.g., PMDM (reaction product of pyromellitic dianhydride (PMDA) and HEMA) and are combined with a second primer, an N-compound that has surface-active properties, e.g., N-phenylglycine or magnesium bis-(N-p-tolylglycine glycidylmethacrylate) [Mg(NTG-GMA)$_2$]. Bonding to dentin with these systems is achieved by conditioning the dentin surface and then coating it with a mixture of the two primers, also called adhesion promoters. The priming resin that is currently used in these bonding systems is PMGDM, which is the addition reaction product of PMDA and glycerol dimethacrylate (Venz and Dickens, 1993; Bowen, 1994). The primer is activated by combining in a dappen dish 40 $\mu$L (two drops) of a 20% solution of PMGDM in acetone and 20 $\mu$L (one drop) of an acetone solution of 5% Mg(NTG-GMA)$_2$. This mixture is brushed onto the conditioned surface. An unfilled bonding resin that may consist of bis-GMA (2,2-bis[p(2'-hydroxy-3'-methacryloxypropoxy)phenylene]propane) and HEMA is placed on the primed surface, thinned with a stream of air and light-cured. A composite resin is adapted to the prepared surface and also light-cured.

In some investigations acidic, carboxylated monomers in combination with other hydrophilic monomers for priming tooth surfaces have been used. Fukushima et al. (1985) reported syntheses of such monomers by reacting 2,2-bis[p (2'-hydroxy-3'-methacryloxypropoxy)phenylene]propane (bis-GMA) and other hydroxylated monomers with the aliphatic succinoxy anhydride resulting in a compound with two aliphatic carboxylic acid groups. Their approach was to use these compounds as primers on dentin and enamel with or without prior conditioning of the tooth surfaces with 37% phosphoric acid. The mean tensile bond strengths between 2 and 12 MPa were considerably lower than shear bond strengths obtainable with the invention presented here.

The 3M company (Minnesota Manufacturing and Mining, St. Paul, Minn.) has developed bonding systems (trade names: Scotchbond®, SB2; SBMP; U.S. Pat. Nos. 4,553, 941 1985; 4,719,149 1988; 4,880,660 1989; 5,554,030 and 5525,648 1996) with primers that contain HEMA and maleic acid. Although maleic acid has a polymerizable functionality, it cannot polymerize without the more reactive HEMA. Therefore, if the maleic acid penetrates into the dentin more deeply than the hydrophilic monomer, the above described phenomenon of nonimpregnated collagen may occur. This incidence has been observed by transmission electron microscopy when Scotchbond 2 was applied to dentin (Dickens-Venz et al., 1992). Since both maleic acid and HEMA are monofunctional monomers, upon polymerization they form a linear polymer.

Organic phosphonates used to promote adhesion to enamel were described by Anbar and Farley (1974), who added vinyl phosphonic acid (VPA) or vinylbenzyl phosphonic acid to composite resins. The authors also claimed that precoating of enamel with a 0.12% neutrazed solution of the said acids improved the bond strength significantly. However, in contrast to the approach taken in this invention, they ensured that the precoating had no etching effect on the enamel.

Acrylated phosphonate esters described for use as adhesion promoting agents for dentin and hard tissues were used as primers and/or admixed with composite resins (Cabasso and Sahni, 1990). The shear bond strengths obtained with such modified composites ranged from 2 MPa to 7 MPa.

A series of primers based on dipentaerythritol-pentaacrylate phosphate esters was developed by Dentsply Int., (trade names: Prisma Universal Bond, PUB, PUB2, PUB 3; U.S. Pat. Nos. 4,514,342, 1985; 4,6657,941 1987; 4,814,423 1989; 4,966,934 1990). These primers are applied to unconditioned dentin. Since they are only weakly acidic compounds, they do not completely remove the smear layer and cause only minor, if any, subsurface demineralization and subsequent formation of hybridized dentin. Mean shear bond strengths of Prisma Universal Bond 2® were reported to be about 7 MPa (Stangel et al., 1994).

The dentin and enamel priming agent of the bonding system Optibond® (Kerr, Santa Ana, Calif.) contains HEMA, a HEMA-phthalate derivative with carboxylic-acid functionality, and glycerophosphate dimethacrylate. This agent is a primer and is applied to acid-etched dentin or enamel (Van Meerbeck et al., 1996). That is, the Optibond® primer acts on already demineralized tooth substrates. In addition, like other priming agents, it remain on the tooth surface, leaving dissolved and loosely bound matter.

There is a need in the art for new methods and compositions for restoring teeth in which the bond strength is good and the time required for the restoration is short.

SUMMARY OF THE INVENTION

It is an object of the invention to provide methods for pre-treating dentin and enamel to improve the bonding to tooth restorations.

It is another object of the invention to provide tooth conditioning compositions.

It is yet another object of the invention to provide kits for restoring teeth.

It is an object of the invention to provide methods of preparing tooth conditioning compositions.

It is yet another object of the invention to provide compounds for use in conditioning teeth.

These and other objects of the invention are provided by one or more embodiments described below. In one embodiment a method for pretreating dentin and enamel of a mineralized tooth is provided. The method comprises the steps of:

applying a conditioner to the dentin and enamel of the tooth, wherein the conditioner comprises a polymerrible acidic monomer which contains at least two carboxylic acid moieties, whereby the dentin and enamel is demineralized; and rinsing the tooth with water to remove soluble components resulting from the demineralization of the dentin and enamel.

In another embodiment of the invention a method for pre-treating dentin and enamel of a mineralized tooth is provided. The method comprises the steps of:

applying a conditioner to the dentin and enamel of the tooth, wherein the conditioner comprises a polymetizable acidic monomer which contains at least two polymerizzble functionalities, such that upon polymerization a cross-linked polymer is formed; and rinsing the tooth with water to remove soluble components resulting from the demineralization of the dentin and enamel.

In another embodiment of the invention a tooth conditioning composition is provided. The tooth conditioning composition comprises:

a polymerizable acidic monomer which contains at least two free carboxylic acid moieties; and vinyl phosphonic acid or vinyl benzyl phosphonic acid.

According to another aspect of the invention a tooth conditioning composition is provided which comprises:

a polymerizable acidic monomer which contains at least two polymerizable functionalities, such that upon polymerization a cross-linked polymer is formed; and vinyl phosphonic acid or vinyl benzyl phosphonic acid.

In yet another embodiment of the invention a kit for repairing teeth is provided. The kit comprises:

a tooth conditioner comprising a polymerizable acidic monomer which contains at least two carboxylic acid moieties;

a primer; and a bonding resin. The primer and bonding resin may be combined in a single formulation.

In yet another embodiment of the invention a kit for repairing teeth is provided. The kit comprises:

a tooth conditioner comprising an acidic polymerizable monomer which contains at least two polymerizable functionalities, such that upon polymerization a cross-linked polymer is formed;

a primer; and a bonding resin. The primer and bonding resin may be combined in a single formulation.

In another aspect of the invention a method of preparing a tooth conditioning composition is provided. The method comprises the step of:

mixing together:
(a) a polymerizable acidic monomer which contains at least two carboxylic acid moieties;
(b) a solvent; and
(c) a stabilizer.

In still another aspect of the invention a method of preparing a tooth conditioning composition is provided. The method comprises the step of:

mixing together:
(a) a polymerizable acidic monomer which contains at least two polymerizable functionalities, such that upon polymerization a cross-linked polymer is formed;
(b) a solvent;
(c) a stabilizer.

According to yet another embodiment of the invention a composition is provided which is formed by reacting a dianhydride with a dihydroxylated dimethacrylate.

These and other embodiments of the invention provide the art with conditioners which have improved bonding strengths to dried dentin and which prevent the collapse of demineralized surface collagen observed when nonpolymerizable mineral acids are used for conditioning.

BRIEF DESCRIPTION OF THE DRAWINGS

FIGS. 6A and 6B: Protective resin (PR) on the dentin reveals the level of the unconditioned dentin surface: drying after conditioning with $H_3PO_4$ resulted in collapsed collagen of about 2 to 3 $\mu$m. In contrast, PMBGA21 protected collagen from collapsing.

FIGS. 7A and 7B: PMBGA21-conditioned surface at high magnification before (a) and after (b) treatment of the ultrathin TEM sections with uranyl acetate.

FIG. 8: Confocal microscopy of dentin treated with fluorescein-labeled PMBGA21 shows that the conditioner, although it was rinsed with water, is present in the hybrid dentin and inside the dentinal tubules.

DETAILED DESCRIPTION OF THE PREFERRED EMBODIMENTS

Figure 1A:
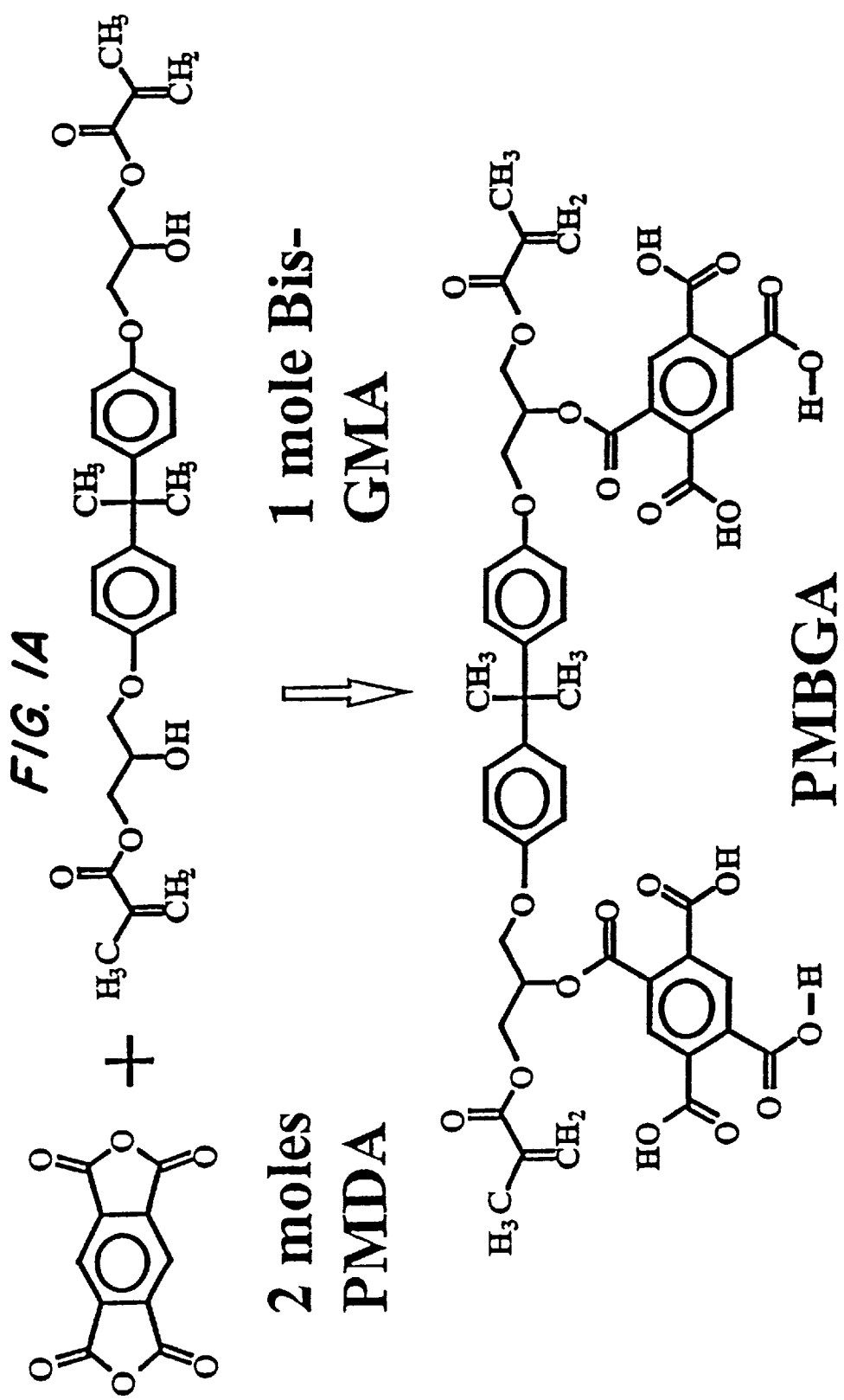
FIGS. 1A–1C: Reaction scheme for the preparation, NMR and FT-IR spectra of PMBGA21, the adduct of pyromellitic dianhydride and bis-GMA.

It is a discovery of the present invention that conditioners for dentin comprising acidic polymerizable monomers simultaneously remove both the smear layer and the subsurface mineral of a mineralized tooth. While not wishing to be bound by theory, it is believed that these conditioners, envelop the mineral-depleted collagen fibers, thus preventing them from collapsing. Because the acid and polymerizable functionalities are within a single molecule, the polymerizable part of the conditioner invariably penetrates to the same depth as the dentin is demineralized. Hence, all demineralized collagen should be impregnated by polymerizable material, eliminating the formation of a zone of nonimpregnated collagen often found between resin-bonded and unaltered dentin. This is important for the long-term stability of the restoration of the tooth. In one preferred embodiment of the invention vinyl phosphonic acid is added to the conditioner, increasing the acidity and ensuring that both dentin and enamel will be sufficiently etched. (Etching of enamel is a process in which surface enamel, unwanted debris, and material with different chemical properties, are selectively removed by an acidic compound, leaving a porous surface.)

In order to condition a tooth, one applies a substance which is capable of demineralizing dentin and enamel. Typically it also removes debris. Similar to the etching of enamel, the conditioning renders the dentin of the tooth more porous to facilitate the bonding between the restoration and the tooth. The conditioner which is applied comprises a polymerizable acidic monomer which contains two or more, and preferably six, carboxylic acid moieties. Alternatively, the conditioner comprises at least two polymerizable functionalities. After the tooth is conditioned for approximately 30–60 seconds, the tooth can be rinsed with water or other dentally acceptable aqueous solvent to remove the water-soluble products of the conditioning, i.e., the mineral and the debris.

After conditioning, a primer and a bonding resin are applied. These can be provided and applied as a single formulation or separately as is desired by the individual practitioner. Polymerization catalysts which will polymerize the conditioner may be contained in the formulation. The monomers of the conditioner will copolymerize with the monomers of the primer and/or the bonding resin. Alternatively, polymerization can be performed prior to the application of the primer and the bonding resin. Suitable catalysts are known in the art and include without limitation the traditional polymerization catalysts for visible light- or chemically initiated free-radical polymerization, such as camphorquinone and aromatic or aliphatic tertiary amines, or an organic peroxide, preferably benzoyl peroxide and camphorquinone.

As mentioned above, a single formulation comprising a primer and bonding resin, can be applied after the enamel and dentin have been conditioned. The use of the single formulation substantially reduces the time needed to complete the procedure. In addition, the single formulation eliminates the possibility of committing errors in confusing the solutions or omitting one of the steps. Even if one uses three consecutive coats of the primer/bonding resin to the tooth, one saves about 60s (or about 20% of the time) compared to applying five coats of a mixture of two primers, and then applying the bonding resin. Moreover, the cost per filling is reduced, as a single solution replaces the two primers and the bonding resin.

The primer portion of the combined primer/bonding resin can be synthesized, for example from 1 mol dianhydride and 2 moles of a mono- or dihydroxylated dimethacrylate resin. The dianhydrides can be selected from those useful for making the conditioner, discussed in detail below. A mono-hydroxylated resin useful in the present invention is glycerol dimethacrylate and a dihydroxylated resin which is useful is Bis-GMA (2,2-bis[p(2'-hydroxy-3'-methacryloxypropoxy) phenylene]propane) or its oligomers. Other primers and bonding resins can be used as are known in the art. Suitable catalysts are known in the art and include without limitation the traditional polymerization catalysts for visible light- or chemically initiated free-radical polymerization, such as camphorquinone and aromatic or aliphatic tertiary amines, or an organic peroxide, preferably benzoyl peroxide and camphorquinone.

Tooth conditioning compositions are also provided by the present invention. According to one embodiment of the invention the tooth conditioning composition contains a polymerizable acidic monomer which contains at least two free carboxylic acid moieties, and preferably four or six free carboxylic acid moieties. Free carboxylic acid moieties are not esterified. According to another embodiment of the invention, the polymerizable acidic monomer contains at least two polymerizable functionalities. The presence of at least two polymerizable functionalities allows the formation of a cross-linked polymeric structure, rather than a purely linear polymer. A preferred polymerizable functionality for a tooth conditioner is a methacrylate functionality. Preferred polymerizable acidic monomers for practice of the present invention have both at least two free carboxylic acid moieties and at least two polymerizable functionalities, such as pyromellitic 2,2 bis-[p(2'-hydroxy-3'-methacryloxypropoxy)phenylene]propane. See FIG. 1C. The tooth conditioning composition may comprise vinyl phosphonic acid, which has been found to increase the bonding strength of the resulting restoration to dentin, presumably due to the increased acidity provided. Vinyl benzyl phosphonic acid may be used instead of vinyl phosphonic acid. Other components of the tooth conditioner of the present invention may be an organic peroxide, such as benzoyl peroxide, and camphorquinone, or a photoreductant such as a tertiary amine and camphorquinone. Stabilizers can also be added to increase shelf life. Stabilizers which may be used include, but are not limited to, butylated hydroxy toluene or methyl ether hydroquinone.

Kits are also provided by the present invention. Kits are packages which typically contain individual reagents for restoring teeth in separate compartments or vessels. Usually kits will be provided with written instructions for using the reagents, either as a package insert or on the boxes, vessels or other compartments. Written instructions can also be provided by reference to another source, such as a journal, Internet web site, or computer diskette, which contains the detailed instructions. One of the kits provided by the present invention is for repairing teeth. Such a kit is provided with a tooth conditioner as fully described herein, as well as at least one primer, and at least one bonding resin. The primer and bonding resins may be pre-combined. Other components of the kit may include a filled composite resin for the complete restoration of the tooth.

According to another aspect of the invention, there is provided here a method of manufacture of a tooth conditioning composition. The method comprises the mixing together of the components as taught herein. Typically these will include a polymerizable acidic monomer which contains at least two carboxylic acid moieties and/or which contains at least two polymerizable functionalities, a solvent, and a stabilizer. Suitable solvents include water, acetone, and ethanol. Suitable stabilizers include butylated hydroxy toluene (BHT) or methyl ether hydroquinone (MEHQ). Other solvents and stabilizers as are known in the art may also be used. As discussed above, vinyl phosphonic acid or vinyl benzylphosphonic acid may be added to improve the bonding strength.

Particularly preferred monomers for formation of the tooth conditioning compositions of the present invention include pyromellitic 2,2 bis-[p(2'-hydroxy-3'-methacryloxypropoxy)phenylene]propane and glycerophosphate dimethacrylate. Other suitable polymerizable acidic monomers which can be used include monomers formed using 1 mol of a dihydroxylated dimethacrylate and 0.5 to 2 moles of a dianhydride, such as pyromellitic dianhydride (chemical name: 1,2,4,5-benzene tetracarboxylic acid dianhydride), 3,4-dicarboxy-1,2,3,4-tetrahydro-1-naphthalenesuccnic acid dianhydride, 3,4,9,10-perylene tetracarboxylic anhydride, bicyclo (2,2,2)-oct-7-ene-2,3,5,6-tetracarboxylic anhydride, 1,4,5,8-naphthalene tetracarboxylic anhydride, 3,3',4,4'-benzophenone tetracarboxylic anhydride, 3,4-3',4'-biphenyl tetracarboxylic anhydride, 1,2,3,4-cyclobutane tetracarboxylic anhydride, 1,2,3,4-cyclopentanetetracarboxylic acid 1,2,3,4-dianhydride, tetrahydrofura,3,4,5-tetracarboxylic anhydride, and Epiclon B4400 tetracarboxylic anhydride. The mono anhydride trimellitic anhydride chloride can also be used. The dihydroxylated dimethacrylate can be Bis-GMA as shown below, or an oligomeric analog thereof, where n>1. The molar ratios of Bis-GMA to dianhydride or anhydride can vary.

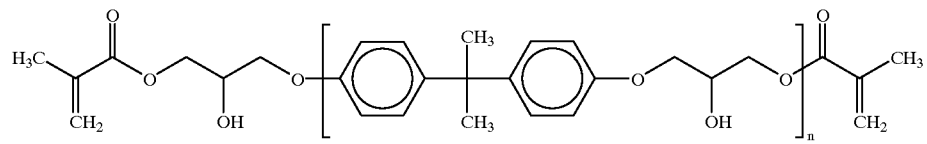

The following examples are provided for exemplification purposes only and are not intended to limit the scope of the invention which has been described in broad terms above.

EXAMPLE 1

The methods used in the examples are described below.
Synthesis

Pyromellitic bis-GMA (2,2-bis[p(2'-hydroxy-3'-methacryloxypropoxy)phenylene]propane) at a molar ratio of two-to-one (PBGA21) was prepared by adding 16.78 g (0.077 moles) of pyromellitic dianhydride (PMDA; Aldrich, Milwaukee, Wis.), to 50 g of a previously dried acetone solution containing 39.4% (0.0385 moles) bis-GMA, Freeman Chemical Corp., Port Washington, Wis.). 3.70 g of Reillex® (Aldrich) were added as reaction catalyst. The mixture was stirred at 45° C. and progress of the reaction was followed by infrared (IR) spectroscopic examination of the acid anhydride absorption. After two weeks, no further changes in the IR spectra were observed, but a small fraction (less than 10%) of unreacted anhydride groups was still present. At this point $H_2O$ was added dropwise to the solution until the remaining anhydride groups were completely converted to carboxylic acid groups. After filtration to remove the catalyst, the product was analyzed by proton nuclear magnetic resonance ($^1$HNMR) and Fourier transform infrared (FT-IR) spectroscopy. The reaction scheme and NMR and FT-IR spectra of the product are shown in FIG. 1.

Dentin Sample Preparation

Dentin samples were prepared and tested by following procedure, as outlined by Venz and Dickens (1993). Extracted, noncarious human molars that had been stored in 0.2% sodium azide at 5° C. were cut with a slowly rotating diamond blade (Isomet, Buehler Ltd., Lake Bluff, Ill.) under running water until a smooth dentin surface was exposed. The teeth were then mounted in a cylindrical polycarbonate holder with a self-curing acrylic and stored in distilled water at room temperature until used for bonding.

Bonding Protocol

One drop of the PMBGA21 conditioning solution was applied to the dentin surface and was agitated for 60 s with a cotton pellet saturated with the same solution. After conditioning, the specimens were rinsed for 1 s to 5 s. In the procedure denoted as "dry," the surfaces were then thoroughly dried with air. For the treatment described as "wet," the surfaces were kept moist under a piece of moist tissue paper until the primer was applied. The priming resin PMGDM, which is the addition product of pyromellitic dianhydride and glycerol dimethacrylate (Venz and Dickens, 1993), was activated by combining 40 μL (two drops) of 20% PMGDM in acetone and 20 μL (one drop) of 5% of the polymerization catalyst, magnesium bis-(N-p-tolylglycine glycidylmethacrylate) [Mg(NTG-GMA)$_2$] in acetone in a dappen dish. Five coatings of the mixture were painted onto the tooth surface, with the acetone being allowed to evaporate between applications. Dual-cure unfilled resin was dabbed on the primed surfaces, thinned with an air stream and light-cured for 20 s with a commercial dental curing light (the MAX Caulk/Dentsply, Miford, Del.). A Teflone®-coated metal iris with an internal diameter of 4 mm was placed directly on the treated surface. The cavity in the iris was filled with composite (API CaulkiDentsply, Milford, Del.), which was then irradiated for 1 min with the curing light. The assembly was left undisturbed for an additional 4 min and then stored in distilled water for 24 h at room temperature prior to testing in shear mode at a cross-head speed of 0.5 mm per min. The teeth were visually examined for pulp exposure after each bonding session. If the pulp horns were exposed, the teeth were replaced before the next bonding cycle.

Two-way analysis-of-variance (ANOVA) and Duncan's multiple range test were used to ascertain significant differences among the data ($p<0.05$).

Microscopic Evaluation

Scanning electron microscopy—For SEM analysis, dentin surfaces were prepared with standardized smear layers, rinsed, and dried. A lightly filled urethane dimethacrylate resin was placed as a narrow line across the smear layer-covered surface to serve as a demarcation indicating the original level of the smear-covered surface before conditioning. The surfaces were then rinsed, dried or kept moist as specified, primed, covered with the lightly filled urethane resin, and cured by a 20 s light exposure. The treated dentin specimens were embedded in epoxy resin, and after curing were sectioned perpendicular to the demarcation line through the center of the tooth. The sectioned halves were then polished under water irrigation, first on silicon carbide paper and finally on felt cloth with 0.25 $\mu$m diamond paste. The polished specimens were mounted on alumina stubs, etched under argon ion for 20 min, sputter-coated with gold in an Ultraspec 90 with etching and coating features (Energy Beam Sciences, Agawam, Mass.) and inspected with a SEM JSM 5300 (JEOL, Peabody, Mass.).

Transmission electron microscopy—The occlusal thirds of human molars were removed within 24 h of extraction and the exposed dentin surfaces were treated with the conditioners H$_3$PO$_4$ and PMBGA21, then dried and primed with a mixture of PMGDM and Mg(NTG-GMA)$_2$ as described in more detail for the shear bond test. After the application of the activated primer, a thin coating of a lightly filled urethane-based dimethacrylate resin was photo polymerized onto the treated surface. The teeth were then prepared for TEM. A block was cut through the center of the treated dentin surface (1 mm×1 mm), fixed in a glutaraldehyde/buffer solution for 3 days to 5 days, stained for 2 h in OsO$_4$, and then subjected to a dehydration/embedding procedure common for TEM. Ultrathin sections of the adhesive/dentin interface prepared with an ultramicrotome (Leica Ultracut S, Reichert, Vienna, Austria) were inspected with a Philips 100 CM TE microscope (Philips, Mahwah, N.J.) at 80 kV.

250 gm thick cuts of specimens that were conditioned with fluorescein-labeled PMBGA21, and then primed as described above were evaluated with a confocal microscope (Bio-Rad, Hercules, Calif.).

Test Procedures

The surface of the teeth were prepared by grinding under water irrigation on 320 grit silicon carbide paper, rinsing and drying.

Figure 2:
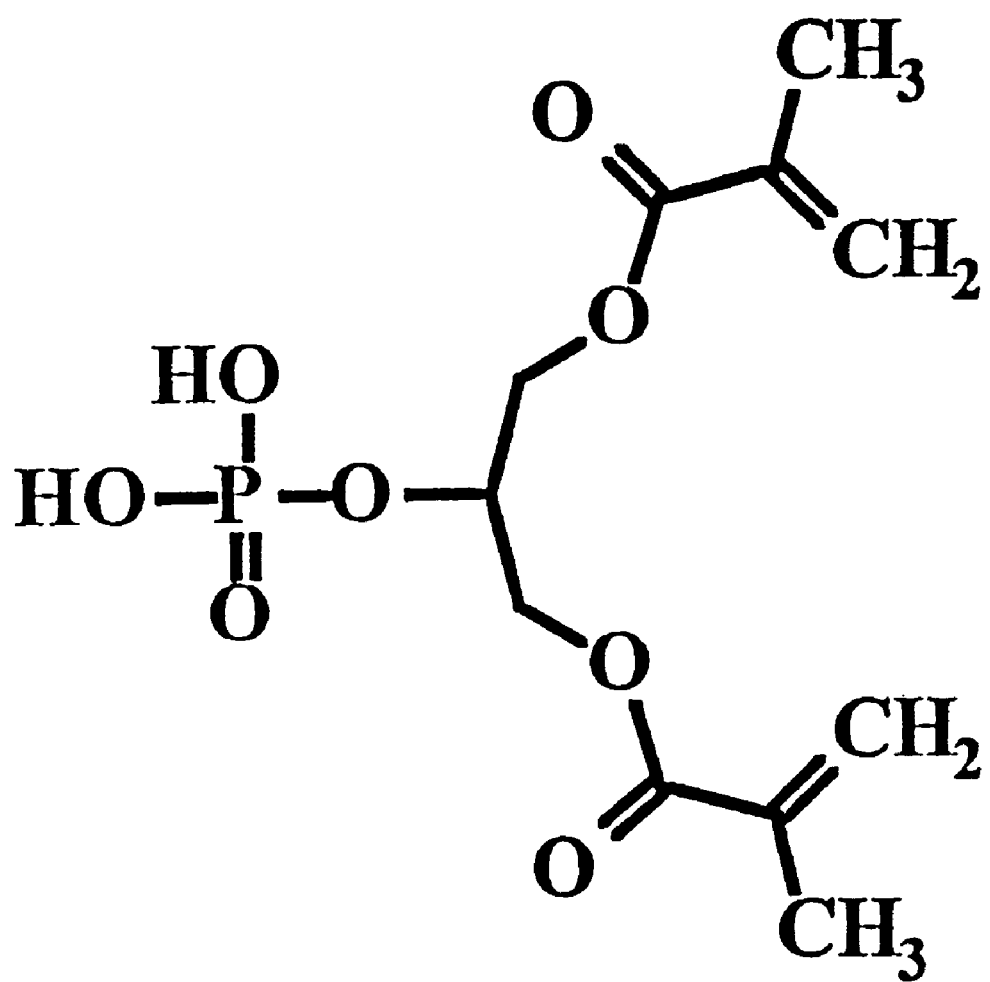
FIG. 2: Structure of glycerophosphate dimethacrylate (glycerophosphate dimethyacrylate)
Figure 1E:
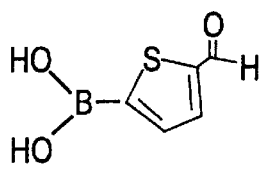
Figure 1E:
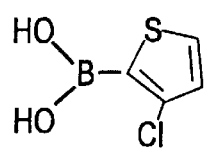
Figure 1E:
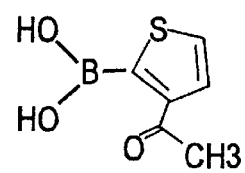
Figure 1E:
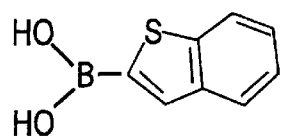
Figure 1E:
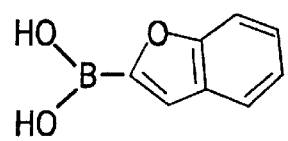
Figure 2A:
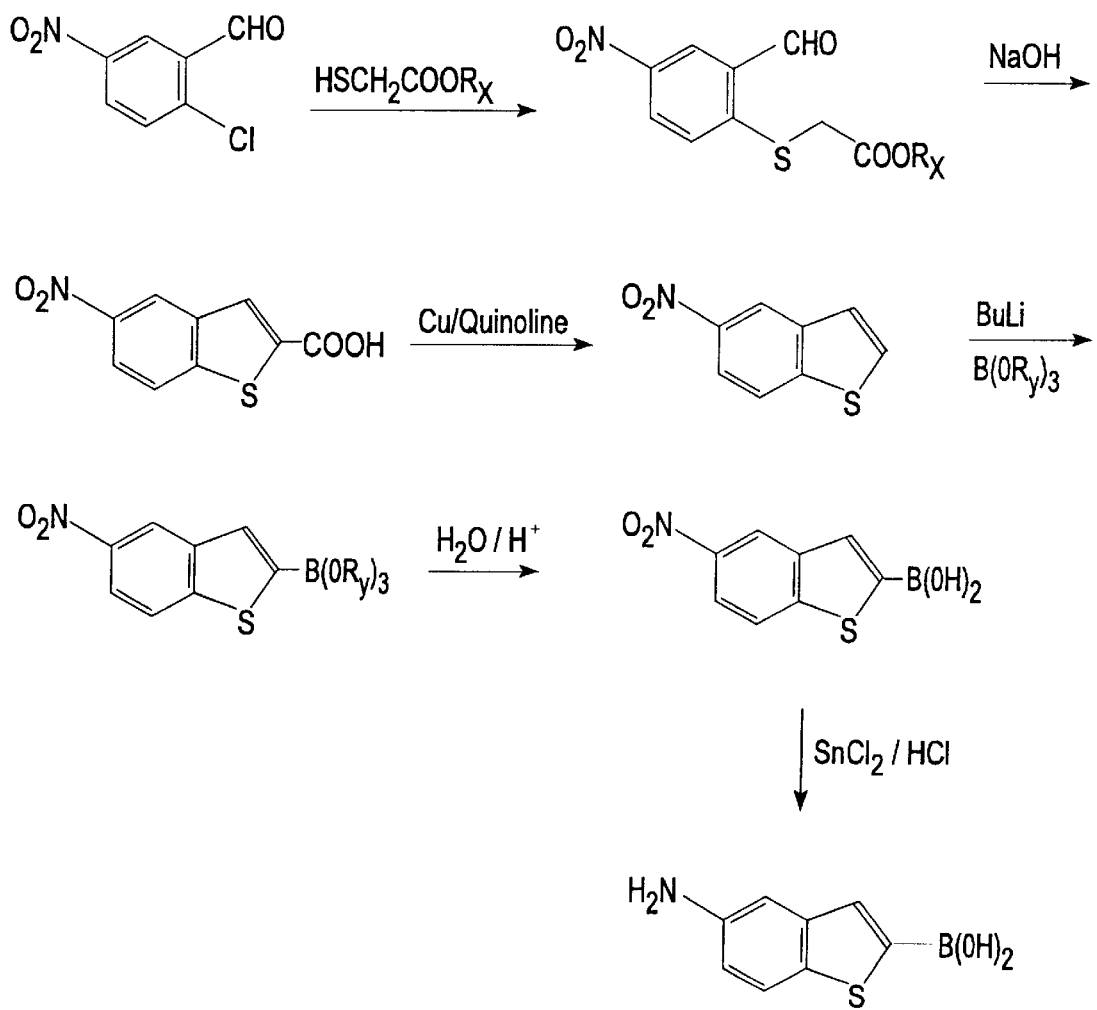
Figure 2B:
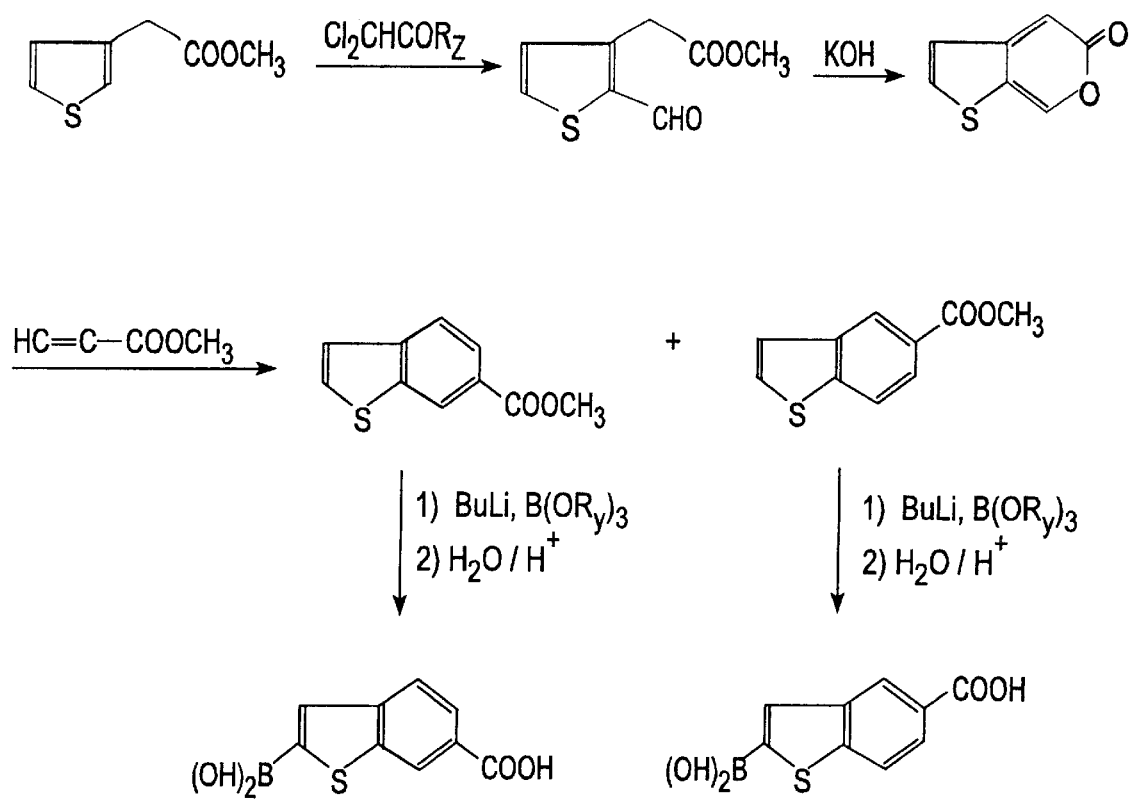
Figure 2C:
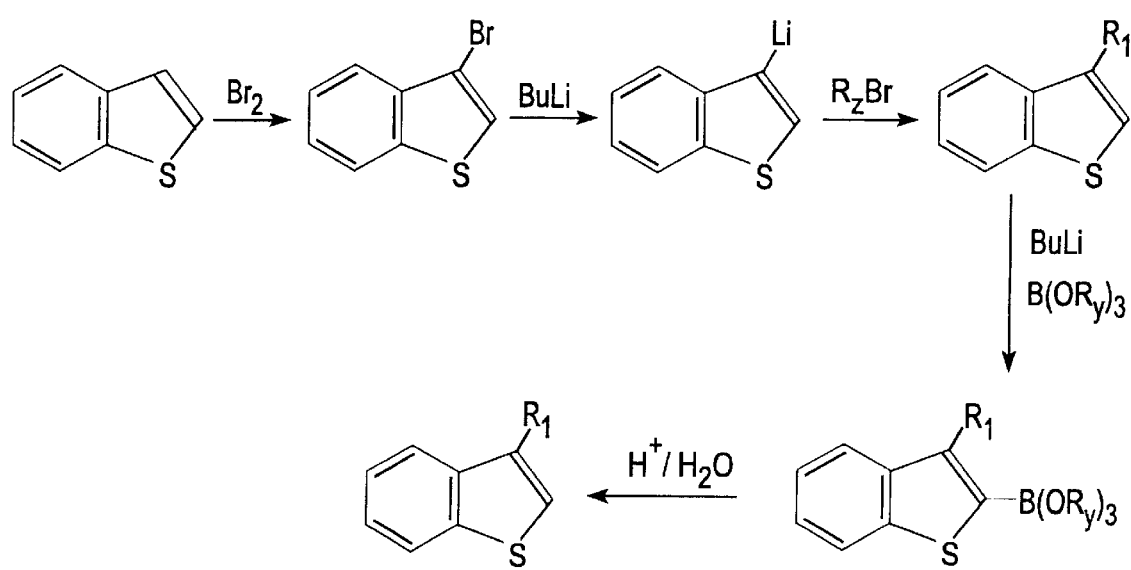

The conditioning was done for 60 seconds with each of the named monomers and for 30 seconds for the control non-polymerizable acid. Pyromellitic bis-[p(2'-hydroxy-3'-methacryloxypropoxy)phenyene]propane (Pyromellitic bis-GMA) was prepared as a 20% solution in acetone/H$_2$O (1:1). Pyromellitic bis-[p(2'-hydroxy-3'-methacryloxypropoxy)phenyene]propane-B was prepared as a 20% solution plus 2% BPO (benzoyl peroxide; mass fraction of resin) in a 1:1 mixture of acetone/H$_2$O. PDM-B (glycerophosphate dimethacrylate; synthesized by reacting glycerol dimethacrylate and phosphorous pentoxide in the presence of triethylamine; see FIG. 2) was prepared as a 20% glycerophosphate dimethacrylate solution of 2% BPO (mass fraction of resin) in acetone/H$_2$O (1:1). The control was a 10% solution of phosphoric acid (H$_3$PO$_4$) gel.

The surfaces were rinsed for 5 seconds with water. They were then dried or kept moist under blotting paper, as indicated in Table 1.

Priming was accomplished by five coats of a mixture of 1 drop (=40 $\mu$l) of 5% Mg(NTG-GMA)$_2$ (Esschem Batch No. 41744) in acetone and 2 drops (=80 $\mu$l) 20% PMGDM in acetone.

Bonding was accomplished using dual cured dimethacrylate resin (Pulpdent Batch No. 120794, 121294). The resin was air thinned and light cured for 20 seconds.

TABLE 1

Results
Contact angles on dry dentin and shear bond strengths (SBS) to dry and moist dentin

| | Dry | | | | Moist | | |
|---|---|---|---|---|---|---|---|
| | Contact Angle with Water | | SBS to dentin (MPa) | | SBS to dentin (MPa) | | |
| Conditioners | mean* | sd* | mean | sd | mean | ± | sd |
| PMBGA21 | 9.1 | ± 3.7 | 34.4[a,b] | ± 5.9 | 44.9[1] | ± | 5.8 |
| PMBGA21-B[#] | — | — | 37.2[a,b] | ± 9.5 | 41.6[a,b] | ± | 12.7 |
| GPDM-B[#] | 35.2 | ± 2.2 | 36.5[a,6] | ± 4.8 | 43.6[a] | ± | 11.0 |
| Control(H$_3$PO$_4$) | 60.2 | ± 1.9 | 30.6[b] | ± 9.1 | 45.3[a] | ± | 9.7 |

*number of specimens = 6; sd = standard deviation
[a,b]unequal letters indicate significant differences, Duncan's grouping, $p < 0.05$
B indicates that benzoyl peroxide was added to the conditioner Shear bond strength data for the four conditioners tested are displayed in Table 1. All SBS tested on moist surfaces were higher than those on dried surfaces. Although two-way analysis for variance (ANOVA) found a significant effect of wet or dry surface conditions ($p<0.001$), Duncan's grouping showed no significant differences for wet or dry conditions for the groups with polymerizable conditioners. The differences between dry and moist conditions in the $H_3PO_4$-treated control group, however, were significant. The mean contact angles of water on conditioned, dried dentin, measured at ambient conditions (23° C. and 46% relative humidity) are also listed in Table 1. For comparison, the mean contact angle (+standard deviation) on dry, smear-covered dentin was 38.2±6.9 (n=10). Keeping the conditioned dentin surfaces moist prior to the measurements resulted in complete spontaneous spreading of water on pyromellitic bis-[p(2'-hydroxy-3'-methacryloxypropoxy) phenylene]propane-conditioned dentin and low water contact angles of less than five degrees for the $H_3PO_4$-conditioned dentin.

Figure 3:
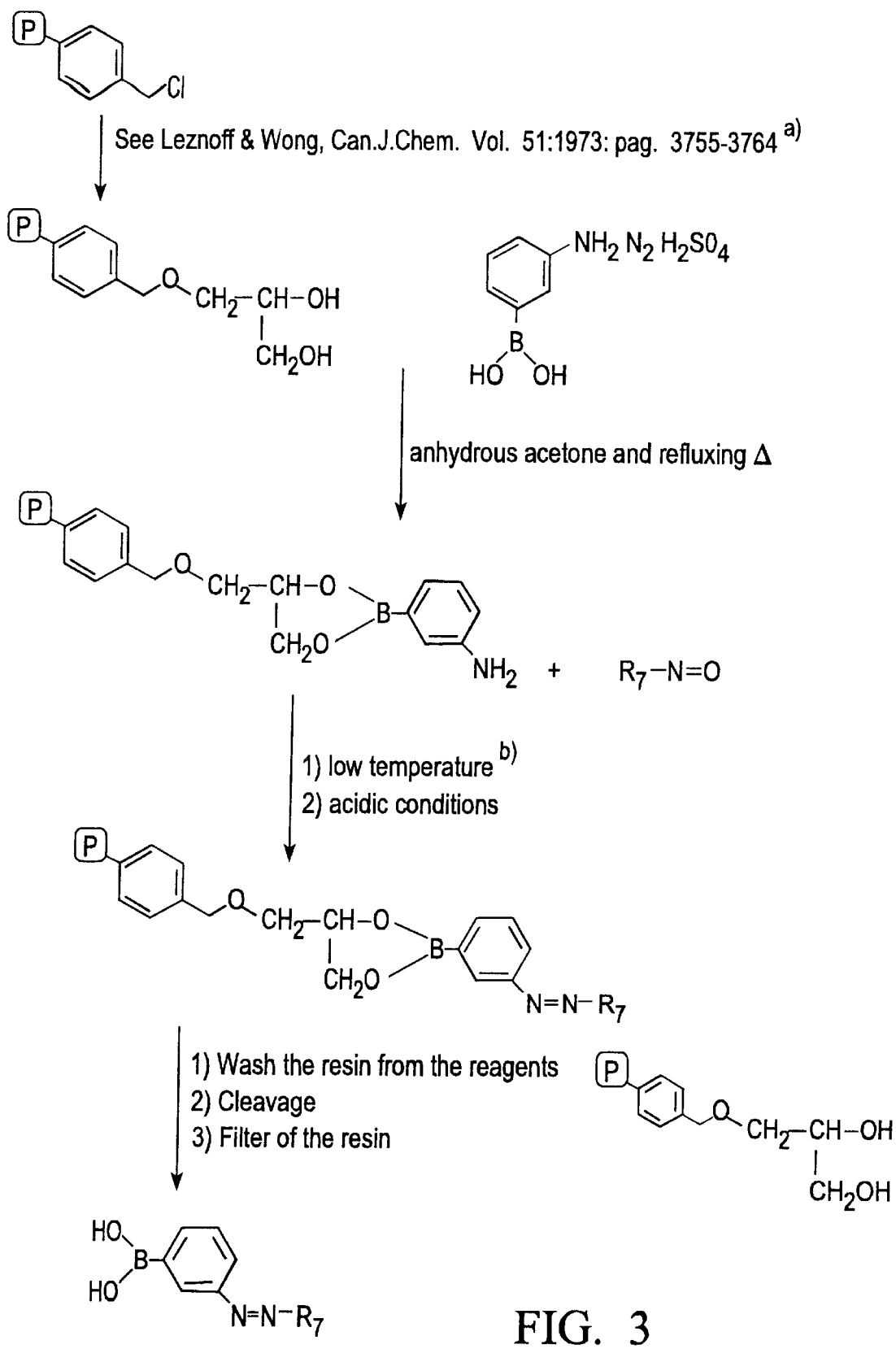
FIGS. 3A–D: Scanning electron micrographs after argon-ion etching of the interfaces of dentin conditioned with $H_3PO_4$ or PMBGA21. Gaps appear between the resin (R) and the hybridized dentin (H) after $H_3PO_4$ treatment and drying. PMBGA21-treatment and drying or wet conditions led to a homogenous transition from 'H' to 'R', indicating good wetting of the demineralized dentin surface.
Figure 4A:
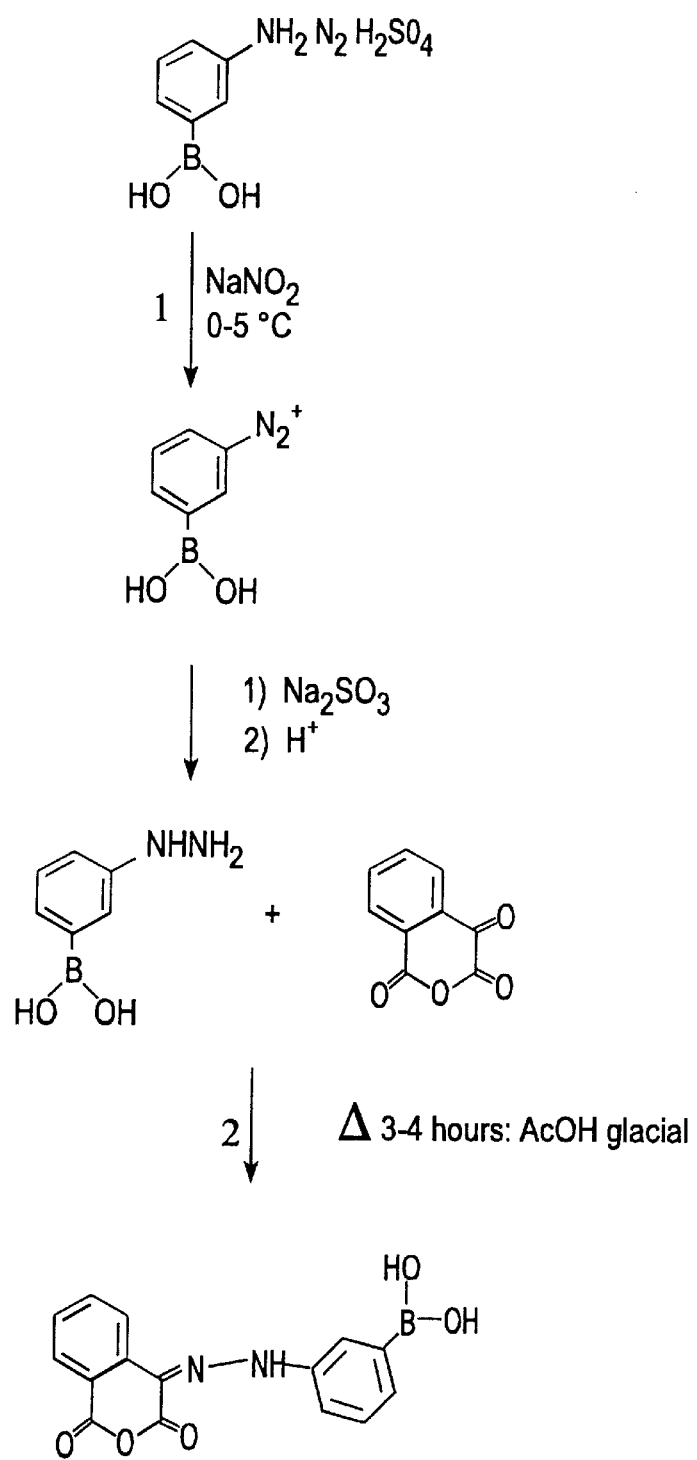
FIG. 4: PMBGA21, when used as conditioner, demineralized the dentin, penetrated into the demineralized surface and formed a resin-inforced "hybrid dentin" (H) with residual mineral-depleted collagen.
Figure 4B:
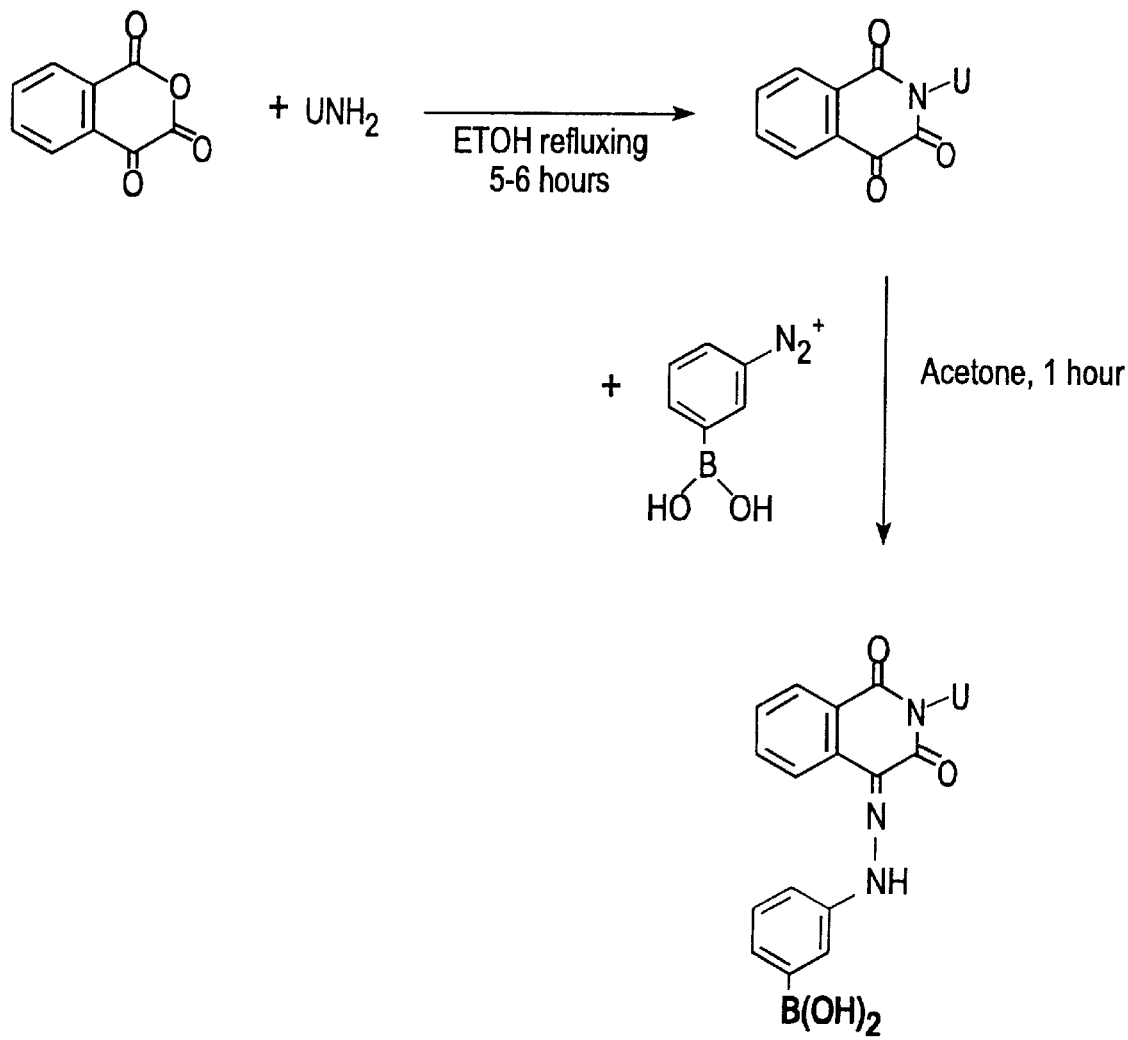
Figure 5:
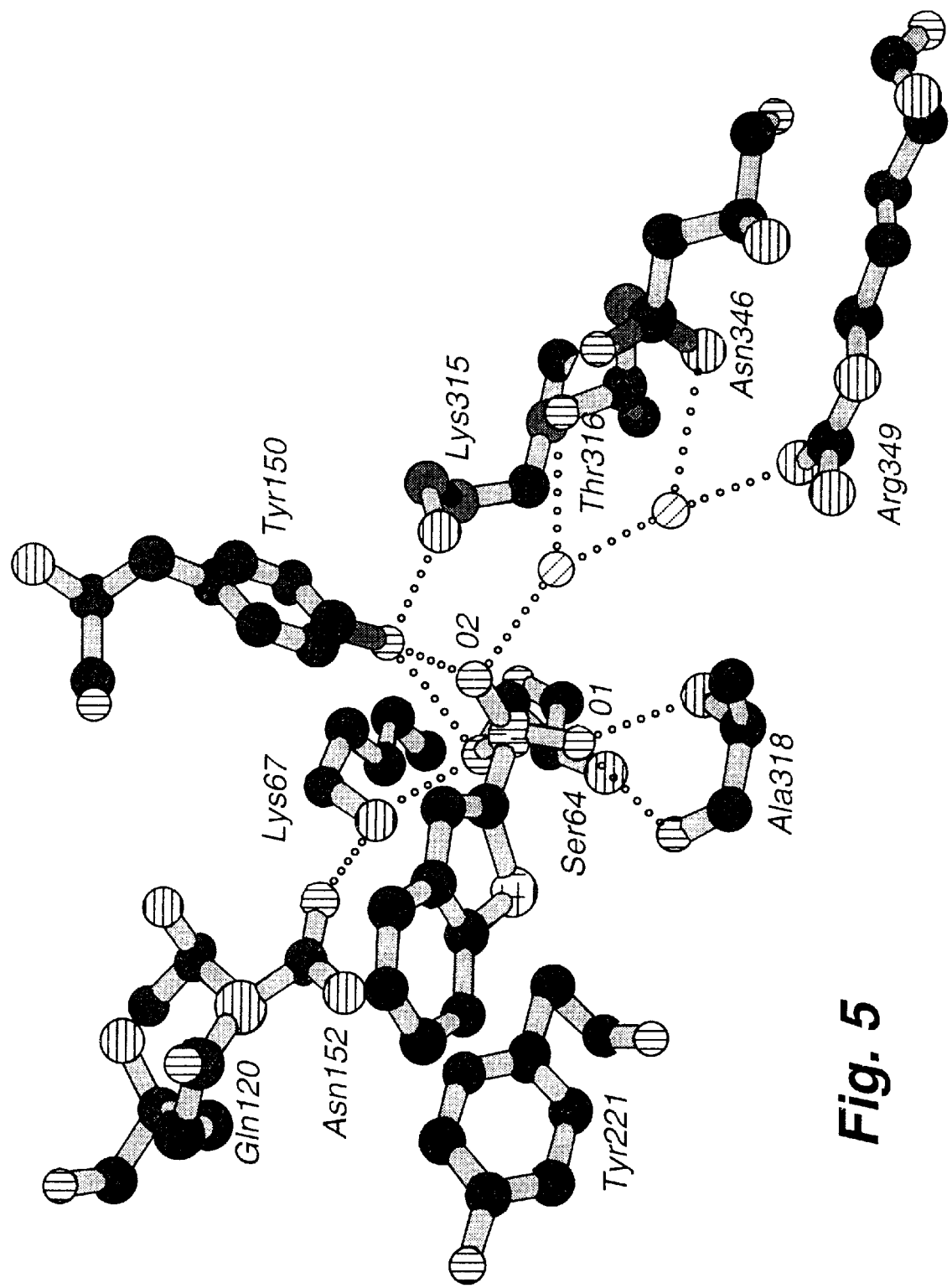
FIGS. 5A and 5B: $H_3PO_4$ conditioned, dried dentin exhibits a dense layer of fused surface collagen (arrow heads). In contrast, PMBGA21-conditioned dentin shows porous surface structures with collagen bundles extended into the overlying resin.

SEM revealed that the polymerizable conditioners partially (pyromellitic bis-[p(2'-hydroxy-3'-methacryloxypropoxy)phenylene]propane) to completely (glycerophosphate dimethacrylate) removed the smear layer on the ground dentin (not shown). Drying dentin after $H_3PO_4$ conditioning (FIG. 3a) caused gaps between the hybrid layer and the bonding resin (arrows). No interfacial gaps were found in specimens conditioned with $H_3PO_4$, but kept moist prior to the priming step FIG. 3b). Some artifactual gaps are present between tubular resin tags and intertubular dentin (FIGS. 3a, b, and d) and inside the unaltered dentin, D, in FIG. 3b. Careful comparison of the surface level of the varnish-protected dentin (thick arrows) to the $H_3PO_4$-conditioned surface, which was primed under moist conditions (thin arrows), revealed a step of about 1–2 μm. SEM of specimens that were conditioned with pyromellitic bis-[p(2'-hydroxy-3'-methacryloxypropoxy)phenylene] propane (FIGS. 3c and d) showed, regardless of wet or dry surface conditions, a hybrid layer that was intimately connected to the overlying primer and/or bonding resin.

Finer details of the resin/hybrid-layer interface were revealed by TEM (FIGS. 4–7). An overview of a pyromellitic bis-[p(2'-hydroxy- 3'-methacryloxypropoxy)phenylene] propane-conditioned surface (FIG. 4) confirms the presence of a hybrid layer, as seen by SEM. The tubular orifices are slightly. finnel-shaped and are obturated by smear plugs, but contrary to mineral conditioned dentin, peritubular dentin has not or only minimally been removed. Higher magnification of a dentin surface conditioned with $H_3PO_4$ showed a dense surface layer of fused collagen FIG. 5a). In contrast, pyromellitic bis-[p(2'-hydroxy-3'-methacryloxypropoxy) phenylene]propane-conditioned dentin, rinsed, dried and primed, shows that the hybrid layer consists to a great extent of partially demineralized dentin and ends in a layer of collagen fibers that extend about 1 μm deep into the primer (FIG. 5b). Medium high magnifications of the same teeth show the areas where the original, untreated dentin surface was protected by a lightly filled dimethacrylate resin (FIGS. 6a and b). Dentin that was demineralized by $H_3PO_4$ and then dried, collapsed by about 2–3 μm and FIG. 6a). Although the pyromellitic bis-[p(2'-hydroxy-3'-methacryloxypropoxy) phenylene]propane-conditioned surface had been rinsed and dried, the collagen did not collapse. On the contrary, it appears that the collagen, which was originally flattened onto the dentin as surface smear, had expanded beyond the surface level (FIG. 6b). FIG. 7 displays a pyromellitic bis-[p(2'-hydroxy-3'-methacryloxypropoxy)phenylene] propane-conditioned interface at high magnification before (a) and after (b) treatment of the ultrathin TEM sections with uranyl acetate. Uranyl acetate is acidic and is known to remove mineral from ultrathin sections during the staining procedure. This effect can be utilized to obtain additional information about the extent of resin envelopment of partially or completely demineralized collagen fibers. If hydroxyapatite crystals in the hybridized region remain after staining with uranyl acetate, as seen in FIG. 7b, their existence can best be explained by assuming that the polymerizable conditioner or the primer had protected the mineral from dissolution.

EXAMPLE 2

Glycerophosphate dimethacrylate (GPDM) was synthesized by reacting phosphorous pentoxide with previously dried glycerol dimethacrylate (GDM) at a molar ratio of 1:1. The product was dried and used as conditioning agent as described above for PMBGA21. The resulting shear bond strengths to dentin are shown in Table 1. No statistical differences were found compared to the control.

EXAMPLE 3

Pyromellitic bis-GMA at a molar ratio of one-to-one (PMBGA11) was prepared by adding 10.07 g (0.046 moles) of PMDA (pyromellitic dianhydride) to 60 g of a previously dried acetone solution containing 39.4 mass % (0.046 moles) bis-GMA. 3.398 g of Reillex® (polyvinyl pyridine or polyvinyl pyrrolidone) were added to this mixture as the reaction catalyst.

EXAMPLE 4

Pyromellitic bis-GMA at a molar ratio of two-to-three (PMBGA23) was prepared by adding 7.1 g (0.033 moles) of PMDA and 25.2 g of bis-GMA (0.049 moles) to 85 g previously dried acetone. 3.2 g of Reillex® (polyvinyl pyridine or polyvinyl pyrrolidone) were added to this mixture as reaction catalyst.

EXAMPLE 5

PMBGA21 was applied to dentin as described above. A single application primer/bonding resin consisting of PMGDM, bis-GMA and HEMA was then applied. A typical primer/resin formulation comprises from 6% to 33% PMGDM, preferredly 33%, from 6% to 12% bis-GMA, preferredly 6%, and from 4% to 8% HEMA (preferredly 4%) dissolved in acetone. Also included are a photoinitiator, a photoreductant, and a free radical stabilizer. The average shear bond strengths for these formulations ranged from 5 MPa to 35 MPa.

EXAMPLE 6

The resulting shear bond strengths for a formulation containing 15% PMGDM, 6% bis-GMA and 4% HEMA are shown in Table 2. Also shown in Table 2 are data obtained with a modified polymerizable conditioning agent. Here, PMBGA21 was mixed with vinyl phosphonic acid (VPA) and applied to dentin and enamel. The resulting shear bond strengths are shown in Table 2. No statistical differences were found between the groups treated with PMBGA21-VPA or $H_3PO_4$ (2-way analysis of variance; Duncan's multiple comparison test; $p<0.05$).

TABLE 2

Shear bond strengths (SBS) to enamel and dentin after conditioning with PMBGA21, PMBGA21-VPA[#] or $H_3PO_4$ followed by application of a single step primer/bonding resin

| Conditioners | SBS to enamel (MPa) | | | SBS to dentin (MPa) | | |
|---|---|---|---|---|---|---|
| | mean | | sd* | mean | | sd |
| PMBGA21 | 27[a,b] | ± | 5 | 17[c] | ± | 6 |
| PMBGA21-VPA | 37[a,b] | ± | 5 | 32[a,b] | ± | 7 |
| Control ($H_3PO_4$) | 40[a] | ± | 11 | 31[a,b] | ± | 10 |

[#]vinyl phosphonic acid;
*standard deviation
[a,b]unequal letters indicate significant differences, Duncan's grouping, $p < 0.05$

EXAMPLE 7

The single step primer/bonding resin was compared to the currently employed multi-step system, comprising $H_3PO_4$ as conditioner, PMGDM and Mg(NTG-GMA)$_2$ as primers and an unfilled bonding resin. The bond strengths in MPa were 27±4 and 28±4, respectively, each estimated from 10 specimens.

EXAMPLE 8

Epiclon B4400-bis-GMA at a molar ratio of two-to-one (B4400BGA) was prepared by adding 20.58 g (0.0780 moles) Epiclon B4400 acid dianhydride (B4400; Dainippon Ink and Chemicals, Inc., Tokyo, Japan) to 44.6 g of previously-dried acetone containing 19.96 g (0.0390 moles) bis-GMA. 4.05 g Reillex® (polyvinyl pyridine or polyvinyl pyrrolidone) were added to this mixture as the reaction catalyst.

EXAMPLE 9

Dentin was conditioned with PMBG21 or $H_3PO_4$, followed by application of a primer and bonding resin. The shear bond strengths to dentin after conditioning were measured. The data are shown in Table 3. The data demonstrate that the combination of the conditioner of the present invention and a single primer/bond application are at least as good as $H_3PO_4$.

TABLE 3

Shear bond strengths (SBS) to dentin after conditioning with PMBGA21 or $H_3PO_4$ followed by application of a multistep or single step primer/bonding resin

| Conditioners | SBS (MPa) with single component primer/bonding resin | | | | SBS (MPa) with multistep primer/bonding resin | | |
|---|---|---|---|---|---|---|---|
| | mean | | sd* | n** | mean | ± sd | n |
| PMBGA21 | 34 | ± | 15 | 3 | | | |
| Control ($H_3PO_4$) | 25 | ± | 4 | 4 | 31 | ± 9 | 4 |

*standard deviation,
**number of specimens; ANOVA found no statistical differences ($p < 0.05$)

References

Anbar M, Fadey EP (1974). Potential use of organic polyphosphonates as adhesives in the restoration of teeth. *J Dent Res* 53:879–888.

Bowen RL (1965). Adhesive bonding of various materials to hard tooth tissues: method of determining bond strength. *J Dent Res* 44:690–695.

Bowen RL, Cobb EN, Rapson JE (1982). Adhesive bonding of various materials to hard tooth tissues: improvement in bond strength to dentin. *J Dent Res* 61:1070–1076.

Bowen RL, Tung MS, Blosser RL, Asmussen E (1987). Dentin and enamel bonding agents. *Int Dent J* 37:158–161.

Bowen RL (1985). Method for obtaining strong adhesive bonding of composites to dentin, enamel and other substrates. U.S. Pat. No. 4,514,527.

Bowen RL (1994). Hydrophilic crosslinking monomers and polymers made therefrom. U.S. Pat. No. 5,320,886.

Cabasso I, Sahni S (1990). Acrylated phosphonate esters containing 1,3-dioxane and 1,3-dioxolane moieties as adhesion-promoting agents for dentin and hard tissues, I. *J Biomed Mater Res* 24:705–720.

Dickens-Venz S, Bowen RL Eichmiller FC (1992). TEM investigation of the dentin-adhesive interface of in vivo and in vitro bonded human teeth. *J Dent Res* 72: Abst. No. 1201

Dickens S (1995): Effects of acid and surface conditions on dentin bond strength and micromorphology. *J Dent Res* 74:Abst. No. 618.

Dickens S (1996): Morphology and bond strength of dentin conditioned with self-etching monomers. *J Dent Res* 75:Abst. No. 2643.

Fukushima T, Kawaguchi M, Inoue Y, Miyazaki K, Horibe T (1985). Application of functional monomers for dental use (part 9)—Syntheses of succinoxy methacrylates and their adhesion to polished and etched tooth surfaces. *J Dent Master* 4: 33–39.

Gwinnett AJ (1992). Moist versus dry dentin: Its effect on shear bond strength. *Am J Dent* 5:127–129.

Gwinnett AJ (1994). Chemically conditioned dentin: A comparison of conventional and environmental scanning electron microscopy findings. *Dent Mater* 10:150–155.

Imai Y, Kadoma K, Kojima K, Akimoto T, Ikakura K, Ohta T (1991): Importance of polymerization initiator systems and interfacial initiation of polymerization in adhesive bonding of resin to dentin. *J Dent Res* 70: 1088–1091.

Inokoshi S, Hosoda H, Haanirattisai C, Shimada Y (1993). Interfacial structure between dentin and seven dentin bonding systems revealed using argon ion beam etching. *Oper Dent* 18:8–16.

Inoue Y, Fukushima T, Miyazaki K (1993). Effect of self-etching primer on bonding of light-cured composite resin to polished dentin. *J Dent Res* 72: Abst. No. 992.

Kanca J (1992). Effect of resin primer solvents and surface wetness on resin composite bond strength to dentin. *Am J Dent* 5:213–215.

Kiyomura M (1987). Bonding strength to bovine dentin with 4-META/MMA-TBB resin. *J Jpn Soc Dent Mater* 6:860–872.

Mizunuma T (1986). Relationship between bond strength of resin to dentin and structural change of dentin collagen during etching-Influence of ferric chloride to structure of the collagen. *J Jpn Dent Mater* 5:54–64.

Nakabayashi N (1982). Resin reinforced dentin due to infiltration of monomers into dentin at the adhesive interface. *J Jpn Dent Mater* 1:78–86.

Nakabayashi N (1985): Bonding of restorative materials to dentin: the present status in Japan. *Int Dent J* 35:145–154.

Nakabayashi N (1995). Watanabe A, Ikeda W (1995). Intra-oral bonding of 4-Meta/MMA-TTB resin to vital human dentin. *Am J Dent* 8:37–42.

Okamoto Y, Heeley JD, Dogon IL, Shintani H (1991). Effects of phosphoric acid and tannic acid on dentin collagen. *J Oral Rehabil* 18:507–512.

Pashley DH; Ciucchi B; Sano H; Horner JA (1993): Permeability of dentin adhesive agents. *Quintess Int.* 24:618–631.

Racean D; Van Scoyoc J; Drummond JL; Steinberg A (1992). Effect of surface treatments on dentin bonding. *Transactions Academy Dent Mater* 5:105–106.

Scott PG, Leaver AG (1974). The degradation of human collagen by trypsin. *Connect Tissue Res* 2:209–307.

Stangel I, Sacher E, Young C, Hanley S (1994). The effect of conditioning on adhesion to human dentin. *Adhesion* 47:133–149.

Swift EJ; Triolo PT (1992). Bond strength of Scotchbond Multi-Purpose to moist dentin and enamel. *Am J Dent* 5:318–320.

Sugizaki J (1991). The effect of the various primers on the dentin adhesion of resin composites, SEM and TEM observations of the resin impregnated layer and adhesion promoting effect of the primers. *Jpn J Conserv Dent* 34: 228–265.

Suh B, Hamer M (1994). Dentin bonding system. U.S. Pat. No. 5,348,988.

Tam LE, Pilliar RM (1994). Fracture surface characterization of dentin-bonded interfacial fracture specimens. *J Dent Res* 73:607–619.

Van Meerbeck B, Inokoshi S, Braem M, Lambrechts P, Vanherie G (1992). Morphological aspects of the resin-dentin interdiffusion zone with different dentin adhesive systems. *J Dent Res* 71:1530–1540.

Van Meerbeck B, Conn LJ, Duke ES, Eick JD, Robinson SJ, Guerrero D (1996). Correlative transmission electron microscopy examination of nondemineralized and demineralized resin-dentin interfaces formed by two dentin adhesive systems. *J Dent Res* 75:879–888.

Venz S, Dickens B (1993). Modified surface-active monomers for adhesive bonding to dentin. *J Dent Res* 72:582–586.

Watanabe I, Nakabayashi N, Pashley DH (1994). Bonding to ground dentin by a phenyl-P self-etching primer. *J Dent Res* 73:1202–1220.

What is claimed is:

1. A kit for repairing teeth, the kit comprising:
   a tooth conditioner comprising a polymerizable acidic monomer which contains at least two carboxylic acid moieties, wherein said monomer comprises a composition formed by reacting (a) a dihydroxylated dimethacrylate and (b) a dianhydride or anhydride chloride;
   a primer; and
   a bonding resin.

2. The kit of claim 1 further comprising a filled composite resin.

3. The kit of claim 1 wherein the polymerizable acidic monomer contains at least two polymerizable functionalities, such that upon polymerization a cross-linked polymer is formed.

4. The kit of claim 3 wherein the polymerizable functionalities are methacrylate functionalities.

5. The kit of claim 3 wherein the primer and the bonding resin are in a single formulation.

6. A kit for repairing teeth, the kit comprising:
   a tooth conditioner comprising a polymerizable acidic monomer which contains at least two carboxylic acid moieties, wherein said monomer comprises a composition formed by reacting (a) a dihydroxylated dimethacrylate and (b) a dianhydride or anhydride chloride;
   a primer; and
   a bonding resin,
   wherein the polymerizable acidic monomer contains at least two polymerizable functionalities, such that upon polymerization a cross-linked polymer is formed and
   wherein the tooth conditioner further comprises:
   vinyl phosphonic acid or vinylbenzylphosphonic acid.

7. The kit of claim 3 further comprising:
   a photoinitiator and a photoreductant.

8. The kit of claim 3 wherein the primer and the bonding resin are in a single formulation.

9. A composition formed by reacting (a) a dihydroxylated dimethacrylate and (b) a dianhydride or anhydride chloride.

10. The composition of claim 9, wherein the dianhydride or anhydride chloride is selected from the group consisting of pyromellitic dianhydride (1,2,4,5-benzene tetracarboxylic acid dianhydride), 3,4-dicarboxy-1,2,3,4-tetrahydro-1-napthalenesuccinic acid dianhydride, 3,4,9,10-perylene tetracraboxylic anhydride, bicyclo (2,2,2)-oct-7-ene-2,3,5,6-tetracarboxylic anhydride, 1,4,5,8-napthalene tetracarboxylic anhydride, 3,3',4,4'-benzophenone tetracarboxylic anhydride, 3,4-3',4'-biphenyl tetracarboxylic anhydride, 1,2,3,4-cyclobutane tetracarboxylic anhydride, 1,2,3,4-cyclopentanetetracarboxylic acid 1,2,3,4-dianhydride, tetrahydrofuran 2,3,4,5-tetracarboxylic anhydride, 3-methyl-3-cyclohexene-1,2-carboxylic anhydride-5-ylsuccinic anhydride, and trimellitic anhydride chloride.

11. A composition formed by reacting (a) a dihydroxylated dimethacrylate and (b) a dianhydride or anhydride chloride, wherein the dihydroxylated dimethacrylate is 2,2-bis {p(2'-hydroxy-3'-methacryloxypropoxyl) phenylene}propane (Bis-GMA).

12. A composition formed by reacting (a) a dihydroxylated dimethacrylate and (b) a dianhydride or anhydride chloride, wherein the dihydroxylated dimethacrylate is an oligomeric analog of 2,2-bis{p(2'-hydroxy-3'-methacryloxypropoxyl)phenylene}propane (Bis-GMA).

13. A composition formed by reacting (a) a dihydroxylated dimethacrylate and (b) a dianhydride or anhydride chloride, wherein the dihydroxylated dimethacrylate is 2,2-bis {p(2-hydroxy-3'-methacryloxypropoxyl) phenylene}propane (Bis-GMA) and the dianhydride is pyromellitic dianhydride.

14. The composition of claim 13, wherein a molar ratio of reactants ranges from 1:2 to 2:1.

15. A composition comprising pyromellitic 2,2 bis-{p(2'-hydroxy-3'-methacryloxypropoxy)phenylene}propane (PMBGA).

16. A kit for repairing teeth, the kit comprising:
    a tooth conditioner comprising a polymerizable acidic monomer which contains at least two carboxylic acid moieties, wherein said monomer comprises a composition formed by reacting (a) a dihydroxylated dimethacrylate and (b) a dianhydride or anhydride chloride;
    a primer; and
    a bonding resin,
    wherein said dianhydride or anhydride chloride is selected from the group consisting of pyromellitic dianhydride (1,2, 4,5-benzene tetracarboxylic acid dianhydride), 3,4-dicarboxy-1,2,3,4-tetrahydro-1-napthalenesuccinic acid dianhydride, 3,4,9,10-perylene tetracraboxylic anhydride, bicyclo (2,2,2)-oct-7-ene-2,3,5,6-tetracarboxylic anhydride, 1,4,5,8-napthalene tetracarboxylic anhydride, 3,3',4,4'-benzophenone tetracarboxylic anhydride, 3,4-3',4'-biphenyl tetracarboxylic anhydride, 1,2,3,4-cyclobutane tetracarboxylic anhydride, 1,2,3,4-cyclopentanetetracarboxylic acid 1,2,3,4-dianhydride, tetrahydrofuran 2,3,4,5-tetracarboxylic anhydride, 3-methyl-3-cyclohexene-1,2-carboxylic anhydride-5-ylsuccinic anhydride, and trimellitic anhydride chloride.

17. The kit of claim 16 further comprising a filled composite resin.

18. The kit of claim 16, wherein said polymerizable acidic monomer contains at least two polymerizable functionalities, such that upon polymerization a cross-linked polymer is formed.

19. The of claim 18, wherein said polymerizable functionalities are methacrylate functionalities.

20. A kit for repairing teeth the kit comprising:
   a tooth conditioner comprising a polymerizable acidic monomer which contains at least two carboxylic acid moieties, wherein said monomer comprises a composition formed by reacting (a) a dihydroxylated dimethacrylate and (b) a dianhydride or anhydride chloride;
   a primer; and
   a bonding resin,
wherein said dihydroxylated dimethacrylate comprises 2,2-bis {p(2'-hydroxy-3'-methacryloxypropoxyl)phenylene}propane (Bis-GMA).

21. A kit for repairing teeth, the kit comprising:
   a tooth conditioner comprising a polymerizable acidic monomer which contains at least two carboxylic acid moieties, wherein said monomer comprises a composition formed by reacting (a) a dihydroxylated dimethacrylate and (b) a dianhydride or anhydride chloride;
   a primer; and
   a bonding resin,
wherein said dihydroxylated dimethacrylate comprises an oligomeric analog of 2,2-bis {p(2'-hydroxy-3'-methacryloxypropoxyl)phenylene}propane (Bis-GMA).

22. A kit for repairing teeth, the kit comprising:
   a tooth conditioner comprising a polymerizable acidic monomer which contains at least two carboxylic acid moieties, wherein said monomer comprises a composition formed by reacting (a) a dihydroxylated dimethacrylate and (b) a dianhydride or anhydride chloride;
   a primer; and
   a bonding resin,
wherein said dihydroxylated dimethacrylate comprises 2,2-bis {p(2'-hydroxy-3'-methacryloxypropoxyl)phenylene}propane (Bis-GMA) and said dianhydride comprises pyromellitic dianhydride.

23. The kit of claim 22, wherein a molar ratio of said Bis-GMA to said pyromellitic dianhydride ranges from 1:2 to 2:1.

24. A kit for repairing teeth, the kit comprising:
   a tooth conditioner comprising a polymerizable acidic monomer which contains at least two carboxylic acid moieties, wherein said monomer comprises a composition formed by reacting (a) a dihydroxylated dimethacrylate and (b) a dianhydride or anhydride chloride;
   a primer; and
   a bonding resin,
further comprising pyromellitic 2,2 bis-{p(2'-hydroxy-3'-methacryloxypropoxy)pheylene}propane.

* * * * *

UNITED STATES PATENT AND TRADEMARK OFFICE
CERTIFICATE OF CORRECTION

PATENT NO.    : 6,187,838 B1
DATED         : February 13, 2001
INVENTOR(S)   : Sabine H. Dickens It is certified that error appears in the above-identified patent and that said Letters Patent is hereby corrected as shown below:

Drawings,
In the Figures, please replace figures 1D-5 with the following:

FIG. 3A

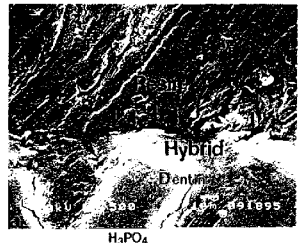

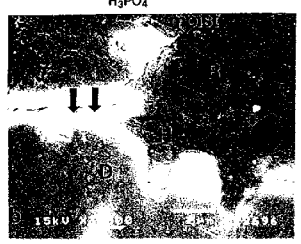

FIG. 3B

In the Figures, please replace figures 1D-5 with the following:

FIG. 3C

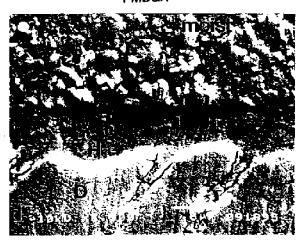

FIG. 3D

UNITED STATES PATENT AND TRADEMARK OFFICE
CERTIFICATE OF CORRECTION

PATENT NO. : 6,187,838 B1 Page 2 of 5
DATED : February 13, 2001
INVENTOR(S) : Sabine H. Dickens It is certified that error appears in the above-identified patent and that said Letters Patent is hereby corrected as shown below:

In the Figures, please replace figures 1D-5 with the following:

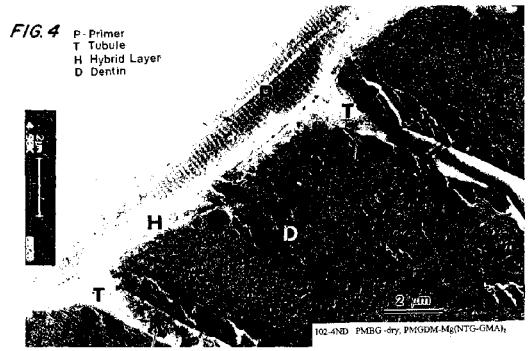

In the Figures, please replace figures 1D-5 with the following:

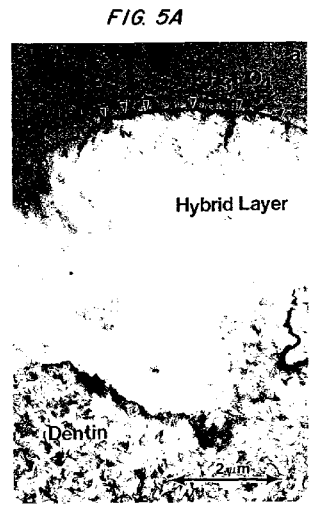

UNITED STATES PATENT AND TRADEMARK OFFICE
CERTIFICATE OF CORRECTION

PATENT NO. : 6,187,838 B1
DATED : February 13, 2001
INVENTOR(S) : Sabine H. Dickens It is certified that error appears in the above-identified patent and that said Letters Patent is hereby corrected as shown below:

In the Figures, please replace figures 1D-5 with the following:

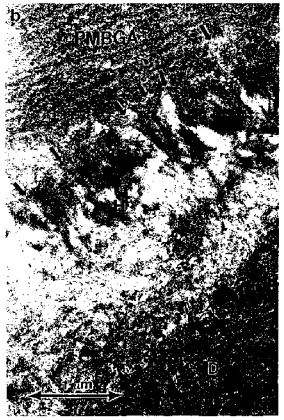

FIG. 5B

In the Figures, please replace figures 1D-5 with the following:

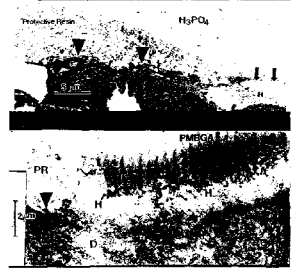

FIG. 6A

FIG. 6B

UNITED STATES PATENT AND TRADEMARK OFFICE
CERTIFICATE OF CORRECTION

PATENT NO.    : 6,187,838 B1
DATED         : February 13, 2001
INVENTOR(S)   : Sabine H. Dickens It is certified that error appears in the above-identified patent and that said Letters Patent is hereby corrected as shown below:

In the Figures, please replace figures 1D-5 with the following:

FIG. 7A

In the Figures, please replace figures 1D-5 with the following:

FIG. 7B

UNITED STATES PATENT AND TRADEMARK OFFICE
CERTIFICATE OF CORRECTION

PATENT NO. : 6,187,838 B1
DATED : February 13, 2001
INVENTOR(S) : Sabine H. Dickens It is certified that error appears in the above-identified patent and that said Letters Patent is hereby corrected as shown below:

In the Figures, please replace figures 1D-5 with the following:

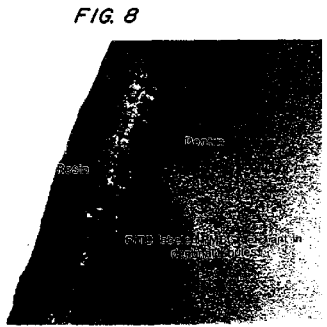

FIG. 8

Signed and Sealed this

Tenth Day of September, 2002

Attest:

JAMES E. ROGAN
Attesting Officer  Director of the United States Patent and Trademark Office